US012788610B2

(12) United States Patent
Stroebech et al.

(10) Patent No.: US 12,788,610 B2
(45) Date of Patent: Nov. 10, 2026

(54) STOMAL SENSOR PATCH

(71) Applicant: Coloplast A/S, Humlebaek (DK)

(72) Inventors: Esben Stroebech, Hoersholm (DK); Richard Morgan Hickmott, Helsingoer (DK)

(73) Assignee: Coloplast A/S, Humlebaek (DK)

( * ) Notice: Subject to any disclaimer, the term of this patent is extended or adjusted under 35 U.S.C. 154(b) by 1314 days.

(21) Appl. No.: 17/620,123

(22) PCT Filed: Jun. 23, 2020

(86) PCT No.: PCT/DK2020/050184

§ 371 (c)(1), (2) Date: Aug. 29, 2022

(87) PCT Pub. No.: WO2020/259775

PCT Pub. Date: Dec. 30, 2020

(65) Prior Publication Data

US 2022/0313472 A1 Oct. 6, 2022

(30) Foreign Application Priority Data

Jun. 24, 2019 (DK) ........................... PA 2019 70396

(51) Int. Cl.

*A61F 5/44* (2006.01)
*A61B 90/00* (2016.01)

(Continued)

(52) U.S. Cl.

CPC ............ *A61F 5/4404* (2013.01); *A61F 5/443* (2013.01); *A61F 5/448* (2013.01); *G01N 27/045* (2013.01);

(Continued)

(58) Field of Classification Search

CPC .......... A61F 5/443; A61F 5/445; A61F 5/448; A61F 5/4404; A61B 2090/0808;

(Continued)

(56) References Cited

U.S. PATENT DOCUMENTS 6,171,289 B1 * 1/2001 Millot ..................... A61F 5/443 604/336
10,874,541 B2 † 12/2020 Seres (Continued)

FOREIGN PATENT DOCUMENTS

WO 2020156624 A1 8/2020
WO 2020156625 A1 8/2020

*Primary Examiner* — Rebecca E Eisenberg
*Assistant Examiner* — Timothy L Flynn
(74) *Attorney, Agent, or Firm* — Coloplast Corp., Coloplast A/S; Nick Baumann

(57) ABSTRACT

Disclosed is a sensor patch and a method for manufacturing a sensor patch for attachment to an adhesive surface of a base plate for an ostomy appliance. The sensor patch having a first side and a second side. The sensor patch being adapted to form a stomal opening with a centre point, the stomal opening being configured to allow passage of output through the stomal opening and into an ostomy pouch attached to a base plate. The sensor patch comprises: a sensor assembly comprising a plurality of electrodes, a first adhesive sensor layer forming the first side of the sensor patch, and a second adhesive sensor layer forming the second side of the sensor patch.

25 Claims, 7 Drawing Sheets

(51) Int. Cl.
*A61F 5/443* (2006.01)
*A61F 5/448* (2006.01)
*G01N 27/04* (2006.01)
*G01N 27/22* (2006.01)

(52) U.S. Cl.
CPC .... *G01N 27/228* (2013.01); *A61B 2090/0808* (2016.02)

(58) Field of Classification Search
CPC .... G01N 27/045; G01N 27/228; G01N 27/06; G01N 27/307
See application file for complete search history.

(56) References Cited

U.S. PATENT DOCUMENTS

| | | | | |
|---|---|---|---|---|
| 2017/0340474 | A1 | 11/2017 | Thirstrup et al. | |
| 2018/0164357 | A1* | 6/2018 | Bernard | G01R 27/26 |
| 2019/0133810 | A1* | 5/2019 | Seres | A61B 5/445 |
| 2022/0304844 | A1* | 9/2022 | Carlsson | A61F 5/4404 |

* cited by examiner
† cited by third party a)

b)

STOMAL SENSOR PATCH

The present disclosure relates to a sensor patch and application thereof to an adhesive base plate for an ostomy appliance. In particular the present disclosure relates to ways of sensing application and/or failure of application of a sensor patch and/r base plate.

BACKGROUND

Stomal output often contains body fluids and visceral contents that are aggressive to both the skin of a user and to ostomy devices, these have a detrimental effect on the efficiency and integrity of the adhesive materials that are applied to attach the ostomy device to the user's skin surface. For users in general safe, reliable and efficient ostomy devices are evidently highly desirable.

However, a particularly major and persistent concern of a large population of ostomists continues to be failure of the base plate adhesive attaching the ostomy appliance to the user's skin surface, because such failure almost inevitably leads to embarrassing and stigmatising leakage incidents. Such incidents in turn are known from several user interviews to lead to a reduced quality-of-life feeling. Adhesive failure of the base plate adhesive can result from various reasons. Most often, a leakage incident is caused by stomal output entering between the proximal surface of the base plate and the user's skin, e.g. due to less-than-optimal attachment of the base plate to the skin arising from e.g. uneven skin surface or skin folds. This undesirable progression of stomal output "underneath" the adhesive leads to deterioration and/or weakening of the adhesive material carrying the weight and providing the seal of the ostomy appliance. Often such failure happens surprisingly fast and is only detectable for the user once the failure has already become so severe that leakage occurs, requiring immediate change of the ostomy appliance and possibly also of the user's clothes.

In other instances, the primary factor of adhesive failure is simply a question of how much time has elapsed since the base plate of the ostomy appliance was first applied to the user's skin surface. In addition to the output from the stoma itself, the peristomal skin surface continuously secretes some moisture (e.g. sweat). To mitigate this, most often adhesives of base plates for ostomy devices include hydrocolloid materials which are capable of absorbing high levels of moisture, thereby stabilizing the polymer matrix of the adhesive material and prolonging the lifetime ("wear time") of the base plate. However, eventually the adhesion capability of the base plate no longer can support the force exerted on the base plate from the load of the output collecting bag, and the appliance must be replaced.

As there can be considerable differences in the severity and/or speed by which adhesive failure and potentially leakage occur, which differences at least to some extent are correlated to various factors including those presented above, a mere indication that failure or leakage is imminent, or that it has already occurred, fails to represent a reliable and satisfactory solution to the problem of avoiding sudden embarrassing and stigmatising leakage incidents in ostomy appliances. In other words, the users of ostomy appliances could greatly benefit from an appliance solution which provides them with better guidance and options regarding how and—not least—how quickly to react to beginning failure or leakage of the adhesive of the base plate of the appliance. More generally, ostomists and health care professionals alike would welcome improvements in ostomy devices to reduce or eliminate the occurrence of sudden leakage incidents.

A problem exist for a sensor patch for application to the adhesive side of a base plate in that the user may attach the sensor patch wrongly, which may cause the sensor patch to be inoperative and/or adversely affect the performance of the base plate. Effectively, a sensor patch being wrongly applied to the base plate can cause both the base plate and the sensor patch to be discarded.

SUMMARY

It is an object of the present disclosure to provide a sensor patch for facilitating reliable and/or improved detection of risk of failure of an ostomy appliance and/or improved detection of risk of leakage. The disclosed sensor patch may be provided to facilitate detection of risk of failure and/or risk of leakage with respect to an adhesive base plate of the ostomy appliance. Furthermore, the disclosed sensor patch may provide for a more failsafe application of the sensor patch to the base plate, i.e. reducing the risk that a user attaches the sensor patch wrongly. For example, the disclosed sensor patch may be provided such that the user does not need to worry about what side of the sensor patch he/she attaches to the base plate and what side of the sensor patch he/she attaches to the skin.

It is a further object of the present disclosure to provide ways of facilitating attachment of a sensor patch to an ostomy appliance, such as a base plate of the ostomy appliance, which reduces the risk of compromising the capability of the ostomy appliance to avoid leakage, in particular between the skin surface of the user and the adhesive surface of the base plate.

Thus, the present disclosure relates to a sensor patch and a method for manufacturing a sensor patch. Accordingly, a sensor patch for attachment to a base plate for an ostomy appliance and a method for manufacturing of such a sensor patch is disclosed.

BRIEF DESCRIPTION OF THE FIGURES

Embodiments of the disclosure will be described in more detail in the following with regard to the accompanying figures. The figures show one way of implementing the present invention and are not to be construed as being limiting to other possible embodiments falling within the scope of the attached claim set.

DETAILED DESCRIPTION

Figure 1:
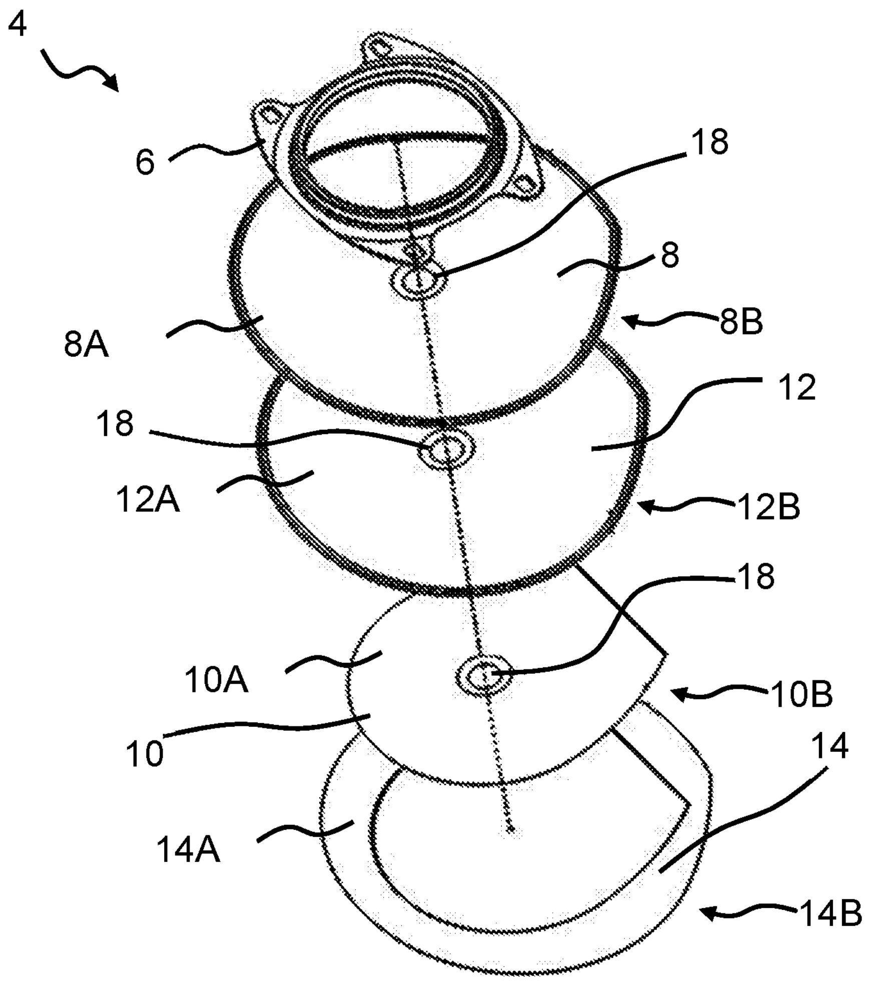
FIG. 1 schematically illustrates an exploded view of an exemplary base plate, FIG. 2 schematically illustrates an exploded view of an exemplary sensor patch, FIG. 3 schematically illustrates an exemplary plurality of electrodes, FIG. 4 schematically illustrates an exemplary sensor assembly, FIG. 5 schematically illustrates an exemplary sensor assembly, FIG. 6*a-b* schematically illustrate cross sections of exemplary sensor assemblies.

In the following Detailed Description, reference is made to the accompanying drawings, which form a part hereof, and in which is shown by way of illustration specific embodiments in which the invention may be practiced. In this regard, directional terminology, such as “top,” “bottom,” “front,” “back,” “leading,” “trailing,” etc., is used with respect to the orientation of the Figure(s) being described. Because components of embodiments can be positioned in a number of different orientations, the directional terminology is used for purposes of illustration and is in no way limiting. It is to be understood that other embodiments may be utilized, and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Throughout this disclosure, the words “stoma” and “ostomy” are used to denote a surgically created opening bypassing the intestines or urinary tract system of a person. The words are used interchangeably, and no differentiated meaning is intended. The same applies for any words or phrases derived from these, e.g. “stomal”, “ostomies” etc. Also, the solid and liquid wastes emanating from the stoma may be referred to as both stomal “output,” “waste(s),” and “fluids” interchangeably. A subject having undergone ostomy surgery may be referred to as “ostomist” or “ostomate”—moreover, also as “patient” or “user”. However, in some cases “user” may also relate or refer to a health care professional (HCP), such as a surgeon or an ostomy care nurse or others. In those cases, it will either be explicitly stated, or be implicit from the context that the “user” is not the “patient” him- or herself.

In the following, whenever referring to proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction is defined as the direction of the stoma, when the appliance is worn by a user. Thus, the axial direction is generally perpendicular to the skin or abdominal surface of the user.

The radial direction is defined as transverse to the axial direction that is transversely to the direction of the stoma, i.e. “across” the distal/proximal surface of the base plate. In some sentences, the words “inner” and “outer” may be used. These qualifiers should generally be perceived with respect to the radial direction, such that a reference to an “outer” element means that the element is farther away from a centre portion of the ostomy appliance than an element referenced as “inner”. In addition, “innermost” should be interpreted as the portion of a component forming a centre of the component and/or being adjacent to the centre of the component. In analogy, “outermost” should be interpreted as a portion of a component forming an outer edge or outer contour of a component and/or being adjacent to that outer edge or outer contour.

The use of the word “substantially” as a qualifier to certain features or effects in this disclosure is intended to simply mean that any deviations are within tolerances that would normally be expected by the skilled person in the relevant field.

The use of the word “generally” as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The use of the word “essentially” as a qualifier to certain structural and functional features or effects in this disclosure is used for emphasizing what is the most important focus of something or fact about something (i.e. a feature may have or fulfil a variety of effects, but when the disclosure discusses one effect as being “essentially” provided, this is the focus and the most important effect in relation to the disclosure).

Throughout the disclosure, the use of the terms “first”, “second”, “third”, “fourth”, “primary”, “secondary”, “tertiary” etc. does not imply any particular order or importance but are included merely to identify individual elements. Furthermore, the labelling of a first element does not imply the presence of a second element and vice versa.

Disclosed is a sensor patch for attachment to a base plate for an ostomy appliance. Such as to facilitate detection of moisture propagation in the adhesive material provided for attaching the base plate to the skin surface of a user as well as detection of increased risk of leakage. For example, the sensor patch may allow electronic measurements of performance of the base plate and/or to facilitate detection of increasing risks of leakage and/or to facilitate detection of decreasing adherence of the base plate to the skin of the user.

The ostomy appliance may comprise a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. For example, the base plate may comprise a coupling ring for coupling an ostomy pouch to the base plate. Further, a two-part ostomy appliance may facilitate correct application of the base plate to skin, e.g. to an improved user sight of the stomal region. Alternatively, the ostomy appliance may be a one-part ostomy appliance, i.e. the base plate and the ostomy pouch may be fixedly attached to each other. The base plate is configured for coupling to a user’s stoma and/or skin surrounding the stoma, such as a peristomal skin area.

The base plate may comprise one or more adhesive layers. The adhesive layer(s) may surround an opening, e.g. a stomal opening. During use, a proximal surface of the adhesive layer(s) adheres to the user’s skin in the peristomal area and/or to additional seals, such as sealing paste, sealing tape and/or sealing ring. The proximal surface of the adhesive layer(s) of the base plate may be configured to adhere to the user’s skin. The distal surface of the adhesive layer(s) may be configured to face away from the skin of the user. The adhesive layer(s) of the base plate may form the adhesive surface of the base plate adapted for attachment of the base plate to the skin surface of the user.

The base plate may comprise a release liner, which may be peeled off by the user prior to applying the base plate to the skin. The release liner may be configured to protect the adhesive layer(s) prior to applying the base plate to the skin. The release liner may comprise a distal surface and a proximal surface. The release liner may be configured to, e.g. prior to applying the base plate to the skin, covering the proximal surface of the adhesive layer(s). The distal surface of the release liner may be configured to, e.g. prior to applying the base plate to the skin, face the proximal surface of the adhesive layer(s).

The base plate may comprise a backing layer. The backing layer may be a protective layer protecting the adhesive layer(s) from external strains and stress during use.

Furthermore, the backing layer may also cover the adhesive layer(s), such that the adhesive layer(s) do not adhere to clothes worn on top of the base plate. The backing layer may comprise a distal surface and a proximal surface. The distal surface of the backing layer may be configured to face away from the skin of the user. The proximal surface of the backing layer may be facing the adhesive layer(s).

The base plate may comprise a stomal opening. Each layer of the base plate may comprise stomal openings for collectively forming the stomal opening of the base plate. The stomal opening may be provided in a centre portion of the base plate. The centre portion of the base plate may be surrounding the stomal opening. The stomal opening may be configured to receive a stoma of the user and/or the stomal opening may be configured to allow output from the stoma to pass through the stomal opening an into an ostomy pouch attached to the base plate. For example, the stomal opening may be configured to allow passage of output from the proximal side of the base plate to a distal side of the base plate. The size and/or shape of the stomal opening may typically be adjusted by the user or nurse before application of the base plate to accommodate the user's stoma.

The sensor patch may have a first side and a second side. The sensor patch is adapted for attachment to the base plate. For example, the sensor patch may be configured to be positioned between the skin of the user and the proximal side of the base plate. For example, the sensor patch may be adapted for attachment to the adhesive layer(s) and/or surface(s) of the base plate. For example, a first side and/or a second side of the sensor patch may be configured to be facing the proximal surface of the adhesive layer(s) of the base plate. For example, the sensor patch, such as the first side and/or the second side of the sensor patch, may be configured to adhere to the proximal surface of the adhesive layer(s) of the base plate.

With the sensor patch of the present disclosure, it may be made unimportant what side of the sensor patch the user decides to apply to the adhesive surface of the base plate and what side of the sensor patch the user applies to the skin surface. Thereby, the risk of applying the sensor patch wrongly may be greatly reduced.

The sensor patch may comprise a stomal opening and/or the sensor patch may be adapted to form a stomal opening. Each layer of the sensor patch, as described below, may comprise stomal openings and/or be adapted to form a stomal opening for collectively forming the stomal opening of the sensor patch. The stomal opening of the sensor patch may be configured to be aligned with the stomal opening of the base plate, such as to collectively form the stomal opening of the combined base plate and sensor patch. The size and/or shape of the stomal opening of the sensor patch may be adjusted by the user or nurse before application of the sensor patch to accommodate the user's stoma. The size and/or shape of the stomal opening of the sensor patch may be adjusted together with adjustment of the stomal opening of the base plate, e.g. after the sensor patch has been attached to the base plate. The stomal opening(s) may have a centre point.

The sensor patch may comprise a sensor assembly comprising a plurality of electrodes including a first electrode and a second electrode for forming a first sensor. The plurality of electrodes may include a third electrode and a fourth electrode forming a second sensor. The sensor assembly may have a first sensor side and a second sensor side. At least a first part of the plurality of electrodes may be exposed on the first sensor side. At least a second part of the plurality of electrodes may be exposed on the second sensor side. The disclosed method may comprise providing the sensor assembly.

The sensor assembly may comprise a support layer, e.g. with a first support surface and a second support surface. The support layer may be a textile fabric. Alternatively, the support layer may be a PU film. In some exemplary sensor patches, the sensor assembly may comprise a plurality of support layers, such as a first support layer and a second support layer. The first support layer and/or the second support layer may be a textile fabric. Alternatively, the first support layer and/or the second support may be a PU film. A support layer, such as the support layer, the first support layer and/or the second support layer, may comprise a first side and a second side, such as a first support surface and a second support surface. For example, the first side of a support layer may be opposite the second side of the same support layer, and/or the first support surface of a support layer may be opposite the second support surface of the same support layer.

The plurality of electrodes may include the first electrode, the second electrode, the third electrode, the fourth electrode, a fifth electrode, a sixth electrode, a seventh electrode, and/or an eighth electrode. One or more electrodes may be a common ground electrode for a plurality of other electrodes. For example, a third sensor may be formed by the first electrode and the fifth electrode, a fourth sensor may be formed by the third electrode and the sixth electrode, a fifth sensor may be formed by the first electrode and the seventh electrode, and/or a sixth sensor may be formed by the second electrode and the eighth electrode. Each electrode may have respective connection parts for connecting the electrodes to respective terminal elements of a monitor device.

The plurality of electrodes is electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

The plurality of electrodes may form loops and/or open loops. Open loop electrode(s) enables electrode arrangement in few or a single electrode layer. For example, the first electrode may form a first loop surrounding the centre point, such as the centre point of a stomal opening of the sensor patch. The second electrode may form a second loop surrounding the centre point. The third electrode may form a third loop surrounding the centre point. The fourth electrode may form a fourth loop surrounding the centre point. A radial distance from the centre point to the second loop may be less than the radial distance from the centre point to the first loop. A radial distance from the centre point to the fourth loop may be less than the radial distance from the centre point to the third loop. A radial distance from the centre point to the third loop may be the same as the radial distance from the centre point to the first loop. A radial distance from the centre point to the fourth loop may be the same as the radial distance from the centre point to the second loop.

A primary first sensor part of the first electrode may be exposed on the first sensor side. A secondary first sensor part of the first electrode may be exposed on the second sensor side. The primary first sensor part may be different from the secondary first sensor part. For example, the primary first sensor part and the secondary first sensor part may be at different longitudinal positions of the first electrode. For example, the first electrode may be alternatingly exposed on the first sensor side and on the second sensor side.

A primary second sensor part of the second electrode may be exposed on the first sensor side. A secondary second sensor part of the second electrode may be exposed on the second sensor side. The primary second sensor part may be different from the secondary second sensor part. For example, the primary second sensor part and the secondary second sensor part may be at different longitudinal positions of the second electrode. For example, the second electrode may be alternatingly exposed on the first sensor side and on the second sensor side.

The first electrode and the second electrode may extend from the first sensor side of the sensor assembly to the second sensor side of the sensor assembly through the support layer. For example, the first electrode and the second electrode may be arranged on the support layer such that the first electrode and the second electrode extend from the first sensor side of the sensor assembly to the second sensor side of the sensor assembly through the support layer. For example, the first electrode may comprise one or more electrically conductive first threads sewn on the support layer, and/or the second electrode may comprise one or more electrically conductive second threads sewn on the support layer. For example, the one or more electrically conductive first threads and/or the one or more electrically conductive second threads may be sewn on the support layer to form the first electrode and/or the second electrode, respectively, extending from the first sensor side of the sensor assembly to the second sensor side of the sensor assembly through the support layer. A support layer of textile fabric may be advantageous if sewing threads to form electrodes. However, other materials may also be used, such as a PU film.

In another exemplary sensor patch, the primary first sensor part of the first electrode may be exposed on the first sensor side and the primary second sensor part of the second electrode may be exposed on the first sensor side. A primary third sensor part of the third electrode may be exposed on the second sensor side and a primary fourth sensor part of the fourth electrode may be exposed on the second sensor side. For example, sensors may be exposed on different sides of the sensor assembly. For example, the first sensor may be exposed on the first sensor side and the second sensor may be exposed on the second sensor side.

The first electrode and/or the second electrode may be arranged on a first side of the support layer. The third electrode and/or the fourth electrode may be arranged on a second side of the support layer, such as the same support layer of which the first electrode and/or the second electrode may be arranged on the first side. For example, the first electrode and/or the second electrode may be printed on the first side of the support layer, i.e. the first electrode and/or the second electrode may be provided as conductive traces on the first side of the support layer. The third electrode and/or the fourth electrode may be printed on the second side of the support layer, i.e. the third electrode and/or the fourth electrode may be provided as conductive traces on the second side of the support layer.

The first electrode and/or the second electrode may be arranged on a first side of the first support layer and the third electrode and/or the fourth electrode may be arranged on a second side of the second support layer. For example, the first electrode and/or the second electrode may be arranged on a different support layer than the third electrode and/or the second electrode. A second side of the first support layer may be arranged to face a first side of the second support layer. For example, the first electrode and/or the second electrode may be arranged on the first support layer, the third electrode and/or the second electrode may be arranged on the second support layer, and the first support layer and the second support layer may be arranged against each other, such that the first electrode and/or the second electrode is exposed on one side and the third electrode and/or the fourth electrode is exposed on the other side. The first support layer and the second support layer may be bonded together, e.g. by welding or by adhesive, such as glue. For example, the second side of the first support layer and the first side of the second support layer may be bonded together, e.g. by welding or by adhesive, such as glue. The first electrode and/or the second electrode may be printed on the first side of the first support layer. The third electrode and/or the fourth electrode may be printed on the second side of the second support layer.

The sensor assembly may comprise a masking element. In some exemplary sensor patches, the sensor assembly may comprise a plurality of masking elements, such as a first masking element and a second masking element. The masking element(s) may be configured to electrically insulate at least parts of the plurality of electrodes from proximal layers, such as the first adhesive sensor layer (as described below) and/or the second adhesive sensor layer (as described below). The masking element may cover or overlap parts of the plurality electrodes, e.g. when seen in the axial direction.

The sensor patch may comprise a first adhesive sensor layer. The first adhesive sensor layer may form the first side of the sensor patch. A primary first side of the first adhesive sensor layer may be adapted for attachment to the skin surface of the user when the sensor patch is used in a first configuration. The primary first side of the first adhesive sensor layer may be adapted for attachment to the adhesive surface(s) of the base plate when the sensor patch is used in a second configuration. A secondary first side of the first adhesive sensor layer may face the sensor assembly, such as the first sensor side of the sensor assembly. The disclosed method may comprise laying out a layer of a first adhesive sensor material for forming the first adhesive sensor layer. Laying out the layer of the first adhesive sensor material for forming the first adhesive sensor layer may comprise extruding the first adhesive sensor layer. Laying out the layer of the first adhesive sensor material for forming the first adhesive sensor layer may comprises moulding, such as injection moulding, of the first adhesive sensor layer. Laying out the layer of the first adhesive sensor material to form the first adhesive sensor layer may comprise laying out the layer of the first adhesive sensor material on a substantially planar surface, such as a release liner.

The sensor patch may comprise a second adhesive sensor layer. The second adhesive sensor layer may form the second side of the sensor patch. A primary second side of the second adhesive sensor layer may be adapted for attachment to the skin surface of the user when the sensor patch is used in the second configuration. The primary second side of the second adhesive sensor layer may be adapted for attachment to the adhesive surface of the base plate when the sensor patch is used in the first configuration. A secondary second side of the first adhesive sensor layer may face the sensor assembly, such as the second sensor side of the sensor assembly. The disclosed method may comprise laying out a layer of a second adhesive sensor material for forming the second adhesive sensor layer. The second adhesive sensor material may be the same material as the first adhesive sensor material. For example, the second adhesive sensor material may be the first adhesive sensor material. Laying out the layer of the second adhesive sensor material for forming the second adhesive sensor layer may comprise extruding the second adhesive sensor layer. Laying out the layer of the second adhesive sensor material for forming the second adhesive sensor layer may comprises moulding, such as injection moulding, of the second adhesive sensor layer. Laying out the layer of the second adhesive sensor material to form the second adhesive sensor layer may comprise laying out the layer of the second adhesive sensor material on a substantially planar surface, such as a release liner.

The sensor assembly may be arranged between the secondary first side of the first adhesive sensor layer and the secondary second side of the second adhesive sensor layer, e.g. such that the first sensor side of the sensor assembly is facing the secondary first side of the first adhesive sensor layer and the second sensor side of the sensor assembly is facing the secondary second side of the second adhesive sensor layer.

The first adhesive sensor material and/or the second adhesive sensor material may comprise one or more polyisobutenes and/or styrene-isoprene-styrene. The first adhesive sensor layer and/or the second adhesive sensor layer may comprise hydrocolloids. For example, the first adhesive sensor material and/or the second adhesive sensor material may comprise hydrocolloids. The hydrocolloids may comprise one or more water soluble or water swellable hydrocolloids. The first adhesive sensor layer and/or the second adhesive sensor layer, such as the first adhesive sensor material and/or the second adhesive sensor material, may be a pressure sensitive adhesive composition suitable for medical purposes comprising a rubbery elastomeric base and one or more water soluble or water swellable hydrocolloids.

The first adhesive sensor layer and/or the second adhesive sensor layer may surround an opening, such as the stomal opening and/or an opening larger than the stomal opening.

The adhesive sensor layer(s) may comprise sensor point openings, to provide an opening between the exterior of the sensor patch and a part of an electrode. Such sensor point openings may be particularly advantageous for leakage sensors for detecting a sudden increase in liquid between the sensor patch and the skin. The first adhesive sensor layer may comprise a plurality of first sensor point openings. Each of the plurality of first sensor point openings may overlap a part, such as a sensor part, of one of the plurality of electrodes to form a sensor point. For example, a primary first sensor point opening may overlap a part, such as a sensor part, of the first electrode and/or of the third electrode. A secondary first sensor point opening may overlap a part, such as a sensor part, of second electrode and/or of the fourth electrode. The second adhesive sensor layer may comprise a plurality of second sensor point openings. Each of the plurality of second sensor point openings may overlap a part, such as a sensor part, of one of the plurality of electrodes to form a sensor point. For example, a primary second sensor point opening may overlap a part, such as a sensor part, of the first electrode and/or of the third electrode. A secondary second sensor point opening may overlap a part, such as a sensor part, of second electrode and/or of the fourth electrode.

The sensor patch may comprise one or more release liners to protect the adhesive surface(s). The disclosed method may comprise providing the one or more release liners. The sensor patch may comprise a first sensor release liner arranged to protect the primary first surface of the first adhesive sensor layer. The sensor patch may comprise a second sensor release liner arranged to protect the primary second surface of the second adhesive sensor layer. The disclosed method may comprise providing the first sensor release liner and/or the second sensor release liner. A release liner, such as the first sensor release liner and/or the second sensor release liner, may be configured to be peeled off by the user. The first sensor release liner and the second sensor release liner may be coupled, e.g. by a coupling release liner part, e.g. extending over an edge of the sensor patch. By coupling the first sensor release liner and the second sensor release liner, the user may use a removed first release liner as a pulling aid in removing the second release liner. For example, the user may remove the first sensor release liner and attach the primary first surface of the first adhesive sensor layer to the base plate or to his skin, and subsequently use the removed first sensor release liner as an aid in removing the second sensor release liner, such as to allow application of the primary second surface of the second adhesive sensor layer to the other of the base plate or the skin.

The release liner(s), such as the first sensor release liner and/or the second sensor release liner, may comprise a plurality of protrusions for maintaining sensor point openings of the adhesive layers. For example, the first sensor release liner may comprise a first plurality of protrusions for extending into the first sensor point openings. The second sensor release liner may comprise a second plurality of protrusions for extending into the second sensor point openings.

Laying out the layer of the first adhesive sensor material for forming the first adhesive sensor layer may comprise laying out the first adhesive sensor material onto the first sensor release liner. Laying out the layer of the first adhesive sensor material for forming the first adhesive sensor layer may comprise scraping the first adhesive sensor material onto the first sensor release liner, e.g. on the second side of the first sensor release liner.

Laying out the layer of the second adhesive sensor material for forming the second adhesive sensor layer may comprise laying out the second adhesive sensor material onto the second sensor release liner. Laying out the layer of the second adhesive sensor material for forming the second adhesive sensor layer may comprise scraping the second adhesive sensor material onto the second sensor release liner, e.g. on the first side of the second sensor release liner.

The sensor patch may comprise a monitor interface. The monitor interface may be configured for electrically and/or mechanically connecting the sensor patch, such as the plurality of electrodes of the sensor patch, to the monitor device. The monitor interface may be configured for wirelessly connecting the sensor patch, such as the electrodes of the sensor patch, to the monitor device. The monitor interface may be configured to electrically and/or mechanically couple the sensor patch and the monitor device.

FIG. 1 schematically illustrates an exploded view of an exemplary base plate 4 of an ostomy appliance. The base plate 4 comprises a first adhesive layer 10 having a distal surface 10A and a proximal surface 10B. During normal use, the proximal surface 10B of the first adhesive layer 10 adheres to the user's skin. The base plate 4 comprises a second adhesive layer 12 having a distal surface 12A and a proximal surface 12B. As illustrated, the second adhesive layer 12 spans a larger surface area than the first adhesive layer 10, such as to provide a rim of the proximal surface 12B of the second adhesive layer 12 surrounding the proximal surface 10B of the first adhesive layer 10.

The base plate 4 comprises a release liner 14, which may be peeled off by the user prior to applying the base plate 4 to the skin. The release liner 14 comprises a distal surface 14A and a proximal surface 14B. The distal surface 14A of the release liner 14 is covering the proximal surface 10B of the first adhesive layer 10 and covering the proximal surface 12B of the second adhesive layer 12 not covered by the first adhesive layer 10. Some exemplary base plates may comprise only the first adhesive layer 10 and not the second adhesive layer 12.

The base plate 4 comprises a backing layer 8. The backing layer 8 is a protective layer protecting the adhesive layers, such as the first adhesive layer 10 and/or the second adhesive layer 12 from external strains and stress during use. Furthermore, the backing layer 8 also covers the adhesive layers, such as the first adhesive layer 10 and/or the second adhesive layer 12, such that the adhesive layers 10,12 does not adhere to clothes worn on top of the base plate 4. The backing layer 8 comprises a distal surface 8A and a proximal surface 8B. The distal surface 8A of the backing layer 8 is configured to face away from the skin of the user. The proximal surface 8B of the backing layer 8 is covering the second adhesive layer 12.

The base plate 4, illustrated in FIG. 1, is a two-part ostomy appliance, thus comprising a coupling ring 6 for coupling an ostomy pouch to the base plate 4, such as to a distal side of the base plate 4. Other exemplary base plates may be provided with the ostomy pouch attached to the base plate, i.e. being a one-piece ostomy appliance.

The base plate 4 comprises a stomal opening 18. The layers of the base plate 4, such as the first adhesive layer 10, the second adhesive layer 12 and the backing layer 8 as illustrated, may comprise stomal openings 18 for collectively forming the stomal opening of the base plate.

Figure 2:
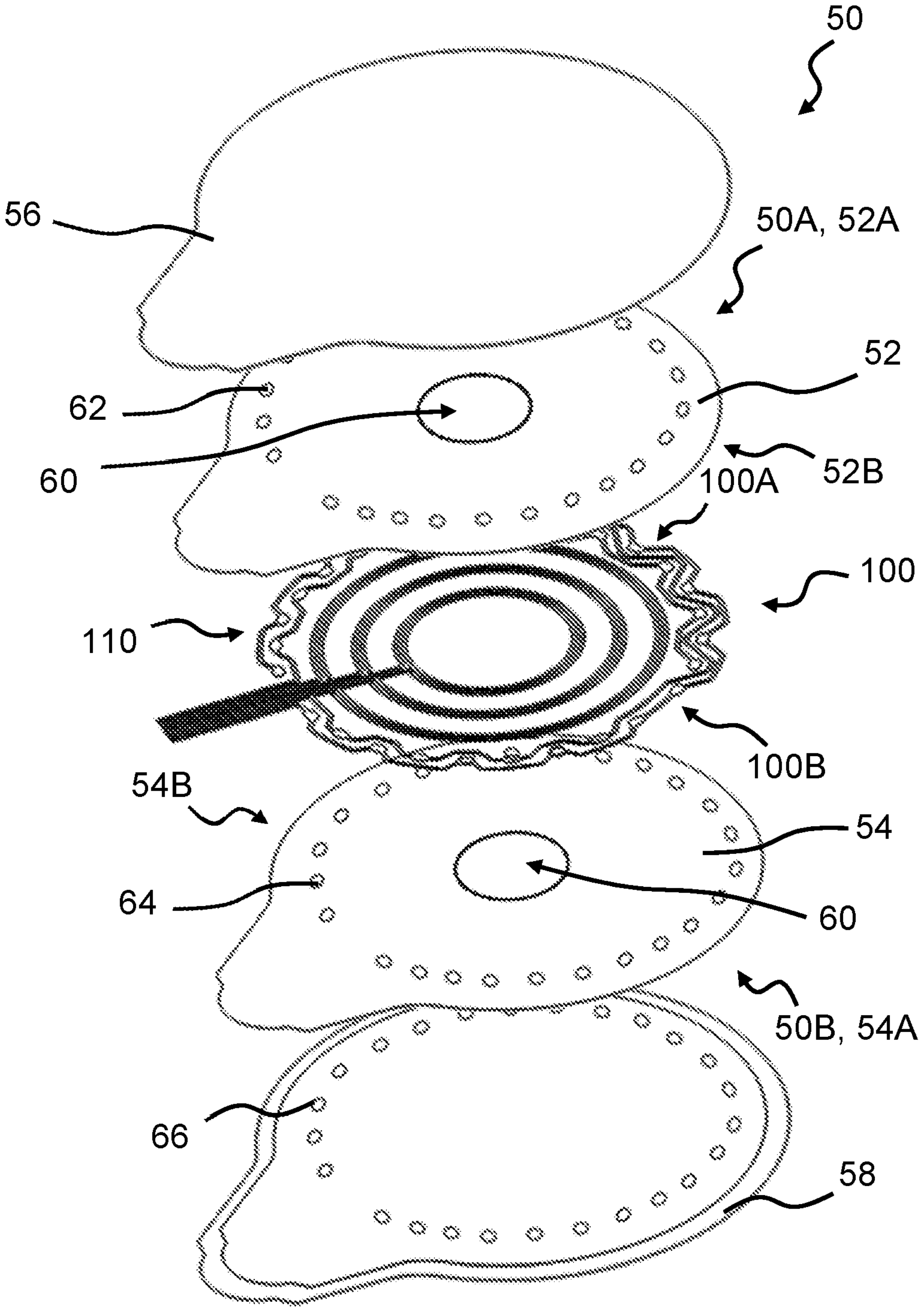

FIG. 2 schematically illustrates an exploded view of an exemplary sensor patch 50, such as a sensor patch 50 being adapted for attachment to a base plate, such as the base plate 4 as illustrated in FIG. 1. The sensor patch 50 is configured to be positioned between the skin of the user and the proximal side of the base plate 4. For example, the sensor patch may be adapted for attachment to the first adhesive layer 10, such as the proximal surface 10B of the first adhesive layer 10, of the base plate 4.

The sensor patch 50 comprises a sensor assembly 100 comprising a plurality of electrodes 110. The sensor assembly 100 has a first sensor side 100A and a second sensor side 100B. At least a first part of the plurality of electrodes 110 are exposed on the first sensor side 100A, and at least a second part of the plurality of electrodes 110 are exposed on the second sensor side 100B. In some exemplary sensor patches some parts of the plurality of electrodes 110 may be exposed on both the first sensor side 100A and the second sensor side 100B. The sensor assembly 100 may form a sensor assembly layer.

The sensor patch 50 comprises a first adhesive sensor layer 52, with a primary first side 52A and a secondary first side 52B. The first adhesive sensor layer 52 is arranged on the first sensor side 100A of the sensor assembly 100, e.g. such that the secondary first side 52B is facing the first sensor side 100A.

The sensor patch 50 comprises a second adhesive sensor layer 54, with a primary second side 54A and a secondary second side 54B. The second adhesive sensor layer 54 is arranged on the second sensor side 100B of the sensor assembly 100, e.g. such that the secondary second side 54B is facing the second sensor side 100B.

When the sensor patch is used in a first configuration, the primary first side 52A of the first adhesive sensor layer 52 is adapted for attachment to the skin surface of the user, and the primary second side 54A of the second adhesive sensor layer 54 is adapted for attachment to the adhesive surface of the base plate. When the sensor patch is used in a second configuration, the primary first side 52A of the first adhesive sensor layer 52 is adapted for attachment to the adhesive surface of the base plate, and the primary second side 54A of the second adhesive sensor layer 54 is adapted for attachment to the skin surface of the user. After being applied to the base plate, the combined base plate and sensor patch 50 forms an adhesive proximal surface configured to be applied to the skin surface of the user. The primary first side 52A of the first adhesive sensor layer 52 and the primary second side 54A of the second adhesive sensor layer may both be adapted for attachment to the skin surface of the user and the adhesive surface of the base plate. Thereby, it may be made unimportant what side the user applies to the adhesive surface of the base plate and what side the user applies to the skin surface, and thus making it easier for the user to use the sensor patch, since the risk of applying the sensor patch wrongly is greatly reduced.

The sensor patch comprises a first sensor release liner 56. The first sensor release liner 56 is arranged to protect the first adhesive sensor layer 52, such as the primary first side 52A of the first sensor adhesive layer 52. The first sensor release liner 56 is configured to be peeled off by the user prior to application of the sensor patch 50 to the base plate and/or prior to application of the combined sensor patch 50 and base plate to the skin. In an exemplary method, the first adhesive sensor layer 52 may be laid out on a surface of the first sensor release liner 56.

The sensor patch comprises a second sensor release liner 58. The second sensor release liner 58 is arranged to protect the second adhesive sensor layer 54, such as the primary second side 54A of the second sensor adhesive layer 54. The second sensor release liner 58 is configured to be peeled off by the user prior to application of the sensor patch 50 to the base plate and/or prior to application of the combined sensor patch 50 and base plate to the skin. In an exemplary method, the second adhesive sensor layer 54 may be laid out on a surface of the second sensor release liner 58.

The sensor patch 50 comprises a stomal opening. The layers of the sensor patch 50, such as the first adhesive sensor layer 52, the sensor assembly 100, and the second adhesive sensor layer 54 may comprise stomal openings 60 for collectively forming the stomal opening of the sensor patch 50. The stomal opening of the sensor patch is configured to be aligned with the stomal opening of the base plate, such as to collectively form the stomal opening of the combined base plate and sensor patch 50.

The first adhesive sensor layer 52 comprises first sensor point openings 62, which may provide openings between the exterior of the sensor patch and parts, such as a sensor parts, of electrodes of the plurality of electrodes 110 of the sensor assembly 100. The second adhesive sensor layer 54 comprises second sensor point openings 64, which may provide openings between the exterior of the sensor patch and parts, such as a sensor parts, of electrodes of the plurality of electrodes 110 of the sensor assembly 100. The release liners 56, 58 comprises a plurality of protrusions 66 for maintaining sensor point openings 62, 64 of the adhesive layers 52, 54, e.g. during storage and transport.

Figure 3:
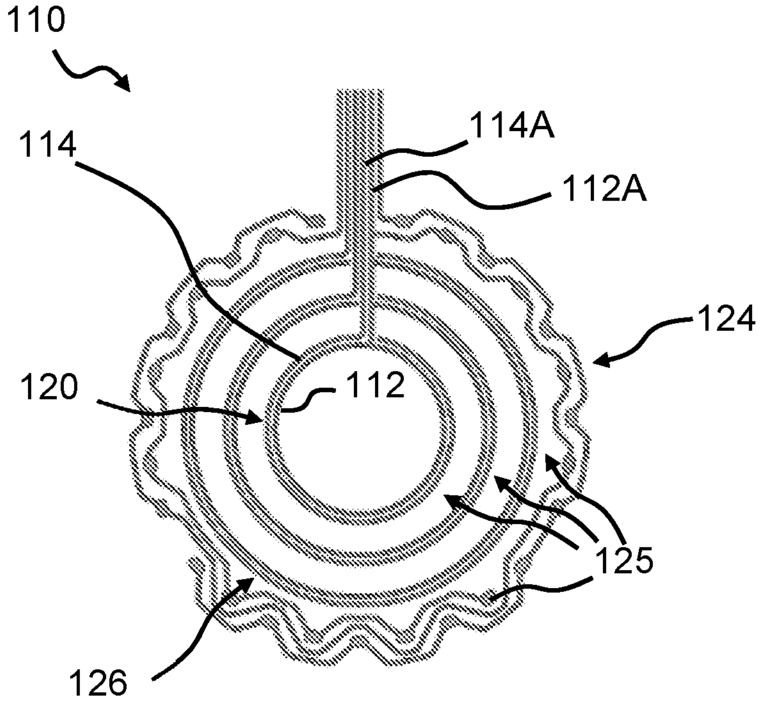

FIG. 3 schematically illustrates an exemplary plurality of electrodes 110. The plurality of electrodes 110 comprises a first electrode 112 and a second electrode 114 for forming a first sensor 120, such as a first sensor 120 configured to sense a change of resistance, conductance and/or capacitance between the first electrode 112 and the second electrode 114, such as by means of a monitor device coupled to the first sensor 120 and applying a voltage. The first electrode 112 comprises a first connection part 112A and the second electrode 114 comprises a second connection part 114A. Other electrodes similarly comprise corresponding connection parts. The connection parts may be utilized for a monitor device to connect to the plurality of electrodes 110.

The plurality of electrodes may comprise leakage sensors 124 and erosion sensors 126. The erosion sensors 126 may be configured to measure and/or indirectly measure the amount of water/moisture in the adhesive, e.g. by measuring resistance between electrode pairs, such between the first electrode 112 and the second electrode 114. The amount of water in the adhesive may be indicative of the performance of the adhesive. Hence, a large amount of water in the adhesive may indicate that it is time to exchange the base plate for continued performance, since excessive amount of water in the adhesive decrease adhesive performance and increase the risk of leakage. The electrodes 110 comprises sensor parts 125 configured for measuring variables, such as resistances, for use in sensing erosion and/or leakage. The leakage sensors 124 comprises designated sensor parts 125 between which potential leakage may be detected, e.g. by a sudden decrease (e.g., short circuit) in resistance between sensor parts, which may be caused by presence of output.

Figure 4:
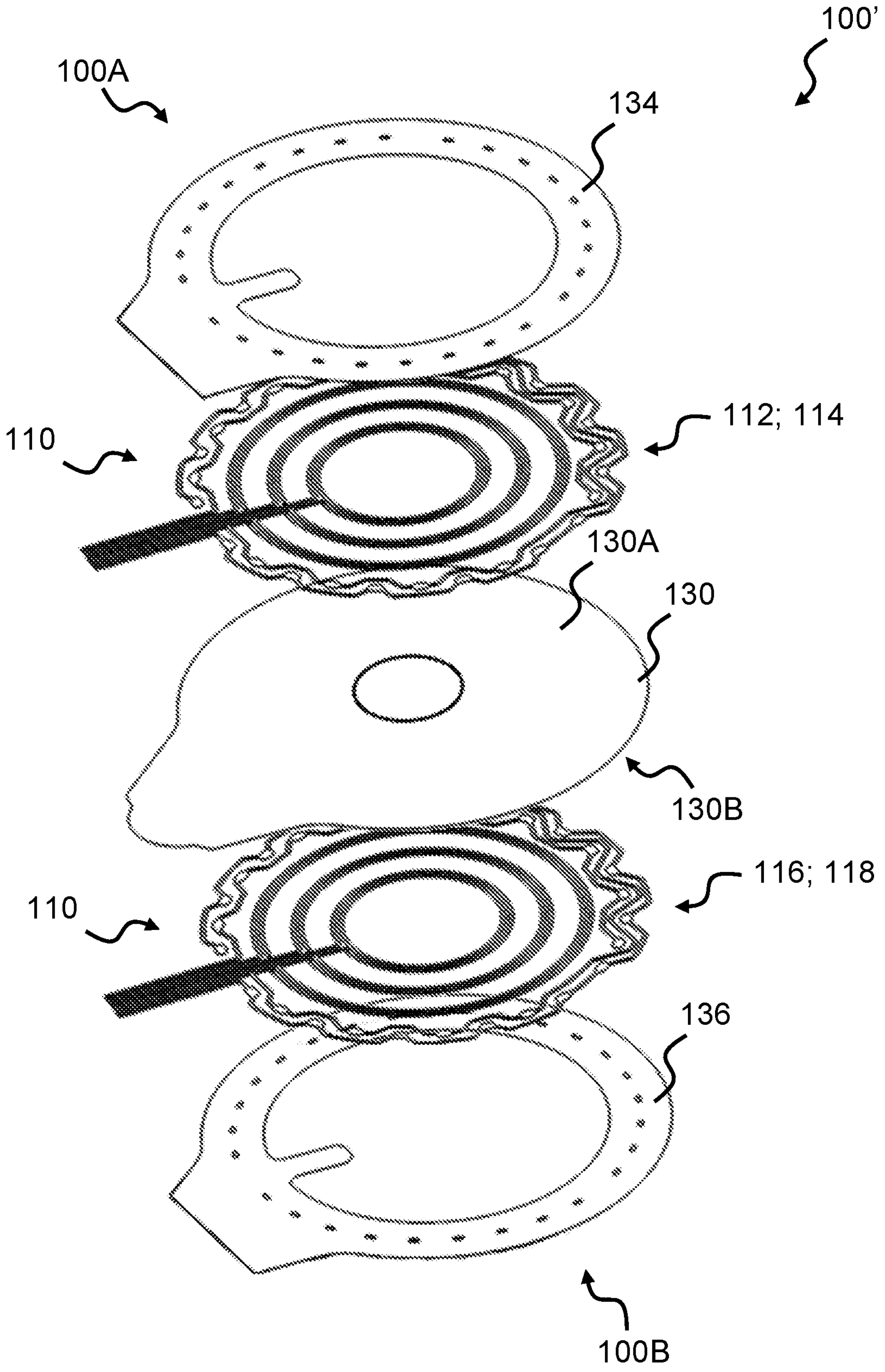

FIG. 4 schematically illustrates an exemplary sensor assembly 100', which may be incorporated as the sensor assembly 100 of the sensor patch 50 of FIG. 2.

The sensor assembly 100' comprises a plurality of electrodes 110, such as the plurality of electrodes 110 as described in respect of FIG. 3, such as two instances of the plurality of electrodes as described in respect of FIG. 3. The plurality of electrodes includes a first electrode 112, a second electrode 114, a third electrode 116 and a fourth electrode 118. The first electrode 112 and the second electrode 114 forms a first sensor. The second electrode 114 and the third electrode forms a second sensor.

The sensor assembly 100' has a first sensor side 100A and a second sensor side 100B. The first electrode 112 and/or a primary first sensor part of the first electrode 112 and the second electrode 114 and/or a primary second sensor part of the second electrode 114 are exposed on the first sensor side 100A. The third electrode 116 and/or a primary third sensor part of the third electrode 116 and the fourth electrode 118 and/or a primary fourth sensor part of the fourth electrode 118 are exposed on the second sensor side 100B.

The electrode assembly 100' comprises a first masking element 134. The first masking element 134 is configured to electrically insulate at least parts of the electrodes 110, such as a first plurality of the plurality of electrodes 110, such as the first electrode 112 and the second electrode 114, from other layers of the sensor patch, such as a first adhesive sensor layer. The first masking element 134 covers or overlap with parts of the first electrode 112 and the second electrode 114 seen in the axial direction.

The electrode assembly 100' comprises a second masking element 136. The second masking element 136 is configured to electrically insulate at least parts of the electrodes 110, such as a second plurality of the plurality of electrodes 110, such as the third electrode 116 and the fourth electrode 116, from other layers of the sensor patch, such as a second adhesive sensor layer. The second masking element 136 covers or overlap with parts of the third electrode 116 and the fourth electrode 118 seen in the axial direction.

For electrodes forming leakage sensors, the masking elements 134, 136 may cover a more substantial part of the electrodes 110, such as to form designated sensor points. For the electrodes forming erosion sensors, the masking elements 134, 136 may leave a more substantial part uncovered. For example, the masking elements 134, 136 may cover the connecting parts of electrodes forming the erosion sensors.

The sensor assembly 100' comprises a support layer, such as a first support layer 130. The first support layer 130 may be a textile or a PU film. The first plurality of the plurality electrodes 110, such as the first electrode 112 and the second electrode 114, are arranged on a first side 130A of the first support layer 130. The second plurality of the plurality of electrodes 110, such as the third electrode 116 and the fourth electrode 118 are arranged on a second side 130B of the first support layer 130, such as on the opposite side of the first plurality of the plurality of electrodes 110. The first electrode 112 and the second electrode 114 may be provided, such as formed, such as printed, on the first side 130A of the first support layer 130. The third electrode 116 and the fourth electrode 118 may be provided, such as formed, such as printed, on the second side 130B of the first support layer 130.

Figure 5:
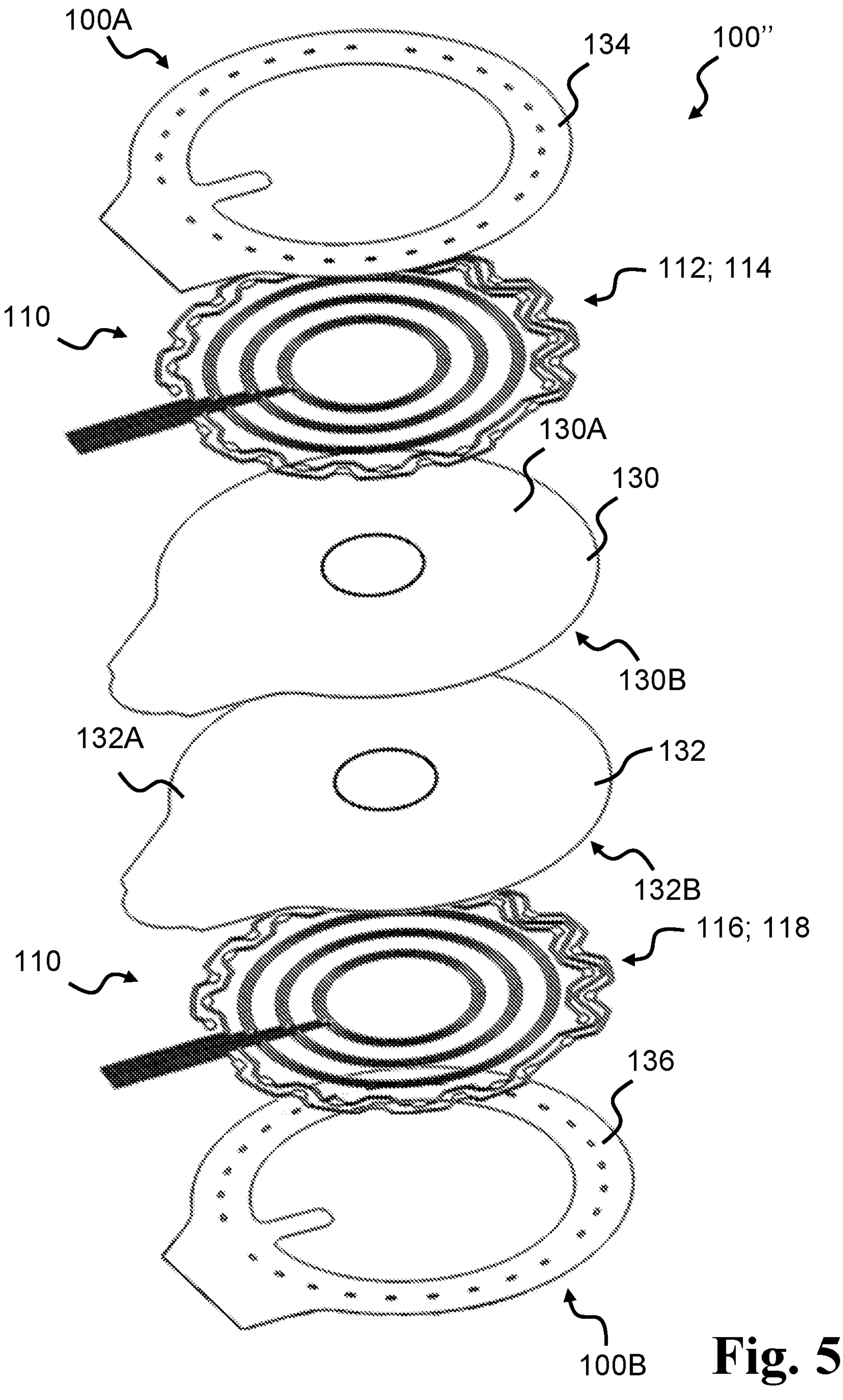

FIG. 5 schematically illustrates an exemplary sensor assembly 100", which may be incorporated as the sensor assembly 100 of the sensor patch 50 of FIG. 2. The sensor assembly 100" comprises the same features as the sensor assembly 100' of FIG. 4, with the difference that the sensor assembly 100" in FIG. 5 comprises an additional support layer, i.e. a second support layer 132. The second support layer 132 may be a textile or a PU film.

The first plurality of the plurality of electrodes 110, e.g. the first electrode 112 and the second electrode 114, are provided on the first support layer 130, e.g. on the first side 130A of the first support layer. The second plurality of the plurality of electrodes 110, e.g. the third electrode 116 and the fourth electrode 118, are provided on the second support layer 132, e.g. on the second side of the second support layer. The second side 130B of the first support layer 130 is arranged to face the first side 132A of the second support layer 132. The second side 130B of the first support layer 130 and the first side 132A of the second support layer 130 may be bonded together. The third electrode 112 and the second electrode 114 may be provided, such as formed, such as printed, on the first side 130A of the first support layer 130. The third electrode 116 and the fourth electrode 118 may be provided, such as formed, such as printed, on the second side 132B of the second support layer 132.

Measurements using the sensor assemblies may be done by a monitor device being electrically coupled to the plurality of electrodes. When employing two sets of electrodes, as exemplified by the sensor assemblies 100', 100" of FIGS. 4 and 5, connecting parts of the two sets of plurality of electrodes may be joined, such that the monitor device is measuring simultaneously on electrodes on both sides of the support layer(s). Alternatively, the monitor device may be configured to identify (e.g. by means of a user input) which of the coupled electrodes are positioned against the skin and/or against the base plate, thereby being able to detect and measure using appropriate electrodes.

Figure 6:
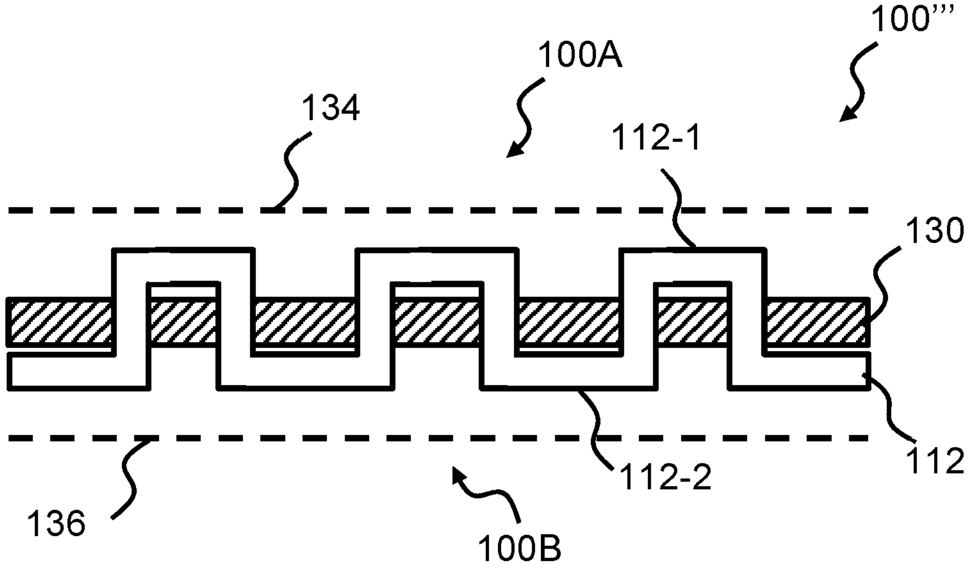
Figure 6:
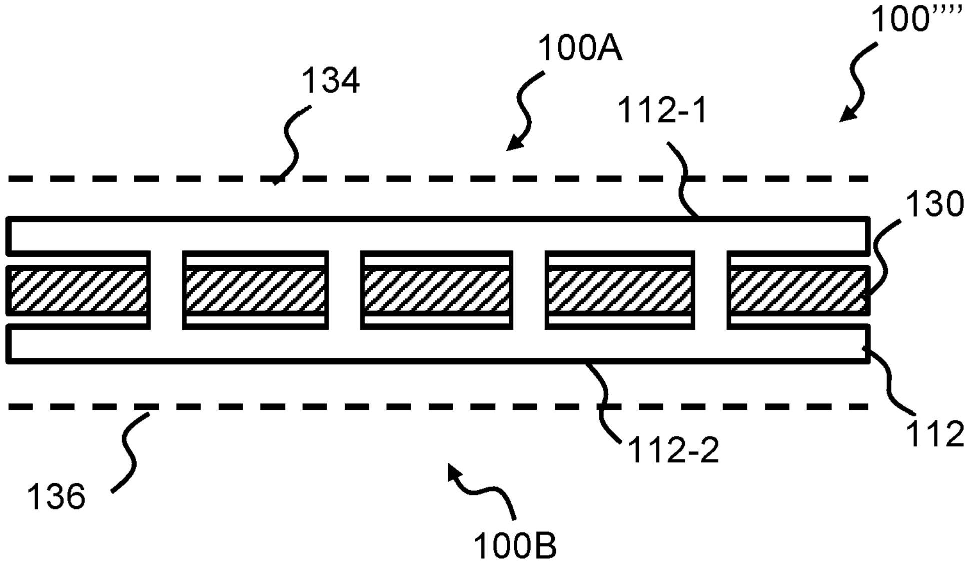

FIG. 6*a-b* schematically illustrate cross sections of exemplary sensor assemblies 100'", 100"", which may be incorporated as the sensor assembly 100 of the sensor patch 50 of FIG. 2. The sensor assemblies 100''', 100'''' comprises the same features as described with respect to the sensor assembly 100' of FIG. 4. However, the sensor assemblies 100''', 100'''' comprises one or more electrodes, such as the first electrode 112 as illustrated, extending through the first support layer 130.

A primary first sensor part 112-1 of the first electrode 112 is exposed on the first sensor side 100A and a secondary first sensor part 112-2 of the first electrode 112 is exposed on the second sensor side 100B. Similarly, although not specifically illustrated, a primary second sensor part of the second electrode may be exposed on the first sensor side 100A and a secondary second sensor part of the second electrode may be exposed on the second sensor side 100B. For example, the first electrode 112 and the second electrode extends from the first sensor side 100A of the sensor assembly 100''', 100'''' to the second sensor side100B through the first support layer 130.

The first electrode 112 may comprise one or more electrically conductive first threads sewn on the first support layer 130. The first electrode 112 may be alternating between being exposed on the first sensor side 100A and the second sensor side 100B as illustrated with sensor assembly 100''' of FIG. 6*a*. Such layout may be obtained, for example, by sewing conductive threads onto the support layer 130 in a manner resembling simple hand-sewing. Alternatively or additionally, the first electrode 112 may provide parts, e.g. similar parts, on each side of the support layer 130 which may be connected through the first support layer 130, as illustrated with sensor assembly 100'''' of FIG. 6*b*. Such layout may be obtained, for example, by sewing conductive threads onto the support layer 130 by a loop stitch.

Providing a sensor assembly as illustrated in FIGS. 6*a-b*, wherein the electrodes extends through the support layer, may allow the measuring, e.g. by a coupled monitor device, to be simplified, since the monitor device does not need to detect or identify which electrodes to use, because the same electrode is able to detect changes in electrical properties, such as resistance, on both sides.

Figure 7:
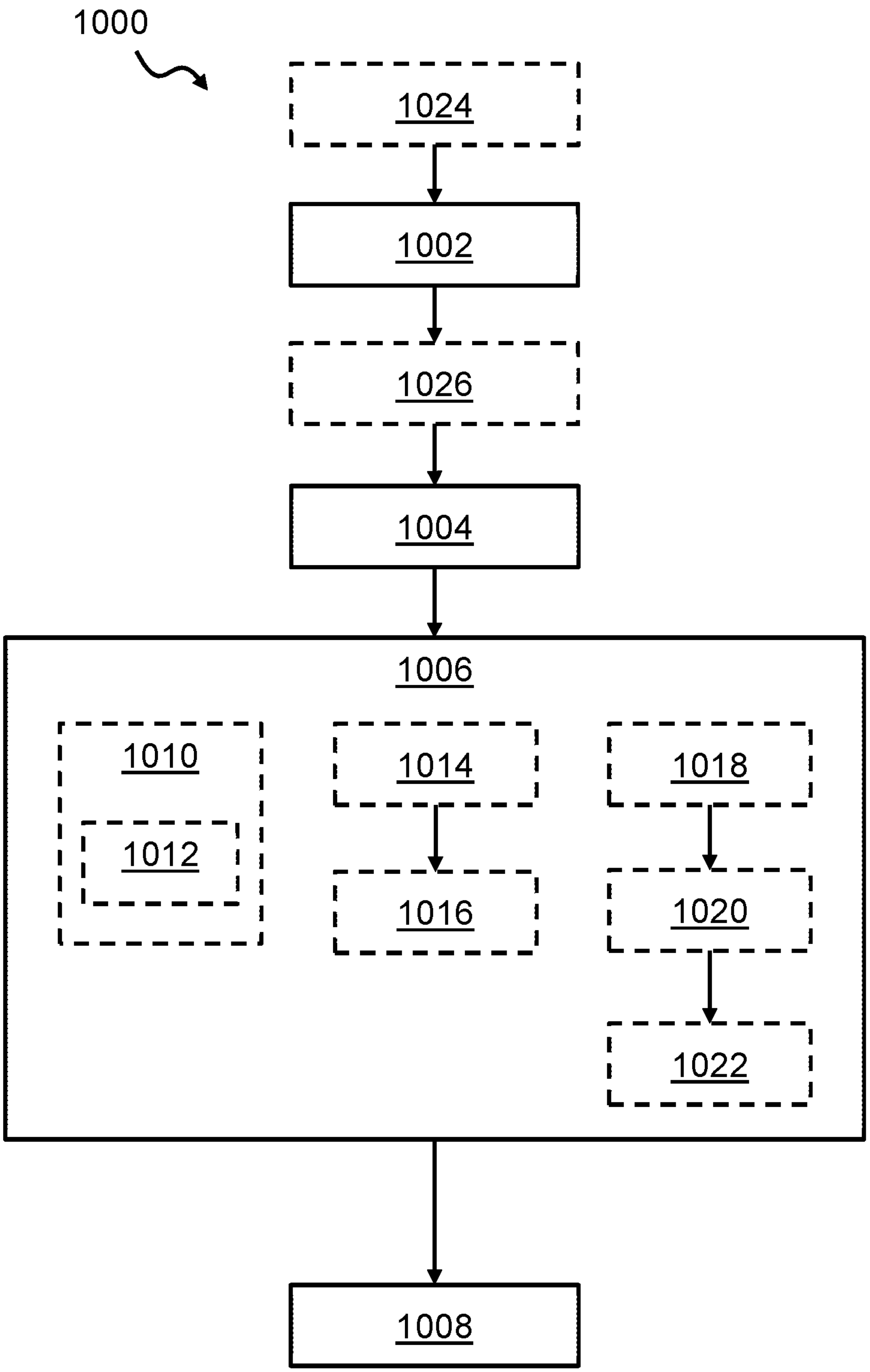
FIG. 7 is a schematic block diagram of an exemplary method.

FIG. 7 is a schematic block diagram of an exemplary method 1000 for manufacturing a sensor patch, such as the sensor patch 50 as described in respect to FIG. 2.

The method 1000 comprises laying out 1002 a layer of a first adhesive sensor material for forming a first adhesive sensor layer of the sensor patch, e.g. such that the first adhesive sensor layer has a primary first side and a secondary first side. Prior to laying out 1002 the layer of first adhesive sensor material, the method 1000 may comprise providing 1024 a first sensor release liner. Laying out 1002 the layer of the first adhesive sensor material may comprise laying out 1002 the layer of the first adhesive sensor material on the first sensor release liner, such as on a second side of the first sensor release liner.

The method 1000 comprises laying out 1004 a layer of a second adhesive sensor material for forming a second adhesive sensor layer of the sensor patch, e.g. such that the second adhesive sensor layer has a primary second side and a secondary second side. Prior to laying out 1004 the layer of second adhesive sensor material, the method 1000 may comprise providing 1026 a second sensor release liner. Laying out 1004 the layer of the second adhesive sensor material may comprise laying out 1004 the layer of the second adhesive sensor material on the second sensor release liner, such as on a first side of the second sensor release liner.

The method 1000 comprises providing 10006 a sensor assembly, such as a sensor assembly as described in relation to any of FIG. 4, FIG. 5, or FIG. 6*a* or 6*b*.

For example, providing 1006 the sensor assembly may comprise arranging 1010 the first electrode and the second electrode on a support layer such that the first electrode and the second electrode extend from the first sensor side of the sensor assembly to the second sensor side of the sensor assembly through the support layer. For example, arranging 1010 the first electrode and the second electrode on the support layer may comprise sewing 1012 one or more electrically conductive threads, e.g. including one or more electrically conductive first threads and/or one or more electrically conductive second threads, on the support layer, to form the first electrode and/or the second electrode extending from the first sensor side of the sensor assembly to the second sensor side of the sensor assembly through the support layer. Thereby a sensor assembly having electrodes exposed on both sides may be obtained.

Alternatively or additionally, providing 1006 the sensor assembly may comprise arranging 1014 the first electrode and the second electrode on a first side of a support layer and arranging 1016 a third electrode and a fourth electrode for forming a second sensor on a second side of the support layer. Thereby a sensor assembly having electrodes exposed on both sides may be obtained.

Alternatively or additionally, providing 1006 the sensor assembly may comprise arranging 1018 the first electrode and the second electrode on a first side of a first support layer and arranging 1020 the third electrode and the fourth electrode on a second side of a second support layer. Providing 1006 the sensor assembly may further comprise bonding together 1022 the second side of the first support layer and the first side of the second support layer. Thereby a sensor assembly having electrodes exposed on both sides may be obtained.

The method 1000 comprises arranging 10008 the sensor assembly between the secondary first side of the first adhesive sensor layer and the secondary second side of the second adhesive sensor layer, e.g. such that the first sensor side of the sensor assembly is facing the secondary first side of the first adhesive sensor layer and the second sensor side of the sensor assembly is facing the secondary second side of the second adhesive sensor layer.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of body side members for ostomy appliances as discussed herein. Therefore, it is intended that this invention be limited only by the claims and the equivalents thereof.

REFERENCES

4 base plate
6 coupling ring
8 top layer
8A distal side/surface of top layer
8B proximal side/surface of top layer
10 first adhesive layer
10A distal side/surface of first adhesive layer
10B proximal side/surface of first adhesive layer
12 second adhesive layer
12A distal side/surface of second adhesive layer

12B proximal side/surface of second adhesive layer
14 release liner
14A distal side/surface of release liner
14B proximal side/surface of release liner
18 stomal opening of base plate
50 sensor patch
50A first side of sensor patch
50B second side of sensor patch
52 first adhesive sensor layer
52A primary first side of first adhesive sensor layer
52B secondary first side of first adhesive sensor layer
54 second adhesive sensor layer
54A primary second side of first adhesive sensor layer
54B secondary second side of first adhesive sensor layer
56 first sensor release liner
58 second sensor release liner
60 stomal opening of sensor patch
62 first sensor point openings
64 second sensor point opening
66 protrusions
100, 100', 100'', 100''' sensor assembly
100A first sensor side
100B second sensor side
110 electrodes
112 first electrode
112-1 primary first sensor part
112-2 secondary first sensor part
112A first connecting part
114 second electrode
114A second connection part
116 third electrode
118 fourth electrode
120 first sensor
122 second sensor
124 leakage sensors
125 sensor part
126 erosion sensors
130 first support layer
130A first side of first support layer
130B second side of first support layer
132 second support layer
132A first side of second support layer
132B second side of second support layer
134 first masking element
136 second masking element
1000 method
1002 laying out layer of first adhesive sensor material
1004 laying out layer of second adhesive sensor material
1006 providing sensor assembly
1008 arranging sensor assembly between adhesive sensor layers
1010 arranging first electrode and second electrode on support layer
1012 sewing electrically conductive thread(s) on support layer
1014 arranging first and second electrode on first side of support layer
1016 arranging third and fourth electrode on second side of support layer
1018 arranging first and second electrode on first side of first support layer
1020 arranging third and fourth electrode on second side of second support layer
1022 bonding together first and second support layer
1024 providing first sensor release liner
1026 providing second sensor release liner

The invention claimed is:

1. A sensor patch for attachment to an adhesive surface of a base plate for a skin surface appliance, the sensor patch having a first side and a second side, wherein the adhesive surface of the base plate is adapted for attachment of the base plate to a skin surface of a user, the sensor patch being adapted to form a stomal opening with a centre point, the stomal opening being configured to allow passage of output through the stomal opening and into a pouch attached to the base plate, the sensor patch comprising:

a sensor assembly comprising a plurality of electrodes including a first electrode and a second electrode for forming a first sensor, the sensor assembly having a first sensor side and a second sensor side, and at least a first part of the plurality of electrodes being exposed on the first sensor side and at least a second part of the plurality of electrodes being exposed on the second sensor side, wherein each sensor of the first part of the plurality of electrodes exposed on the first sensor side corresponds to a sensor of the second part of the plurality of electrodes exposed on the second sensor side, a first adhesive sensor layer forming the first side of the sensor patch, wherein a primary first side of the first adhesive sensor layer is adapted for attachment to the skin surface of the user when the sensor patch is used in a first configuration, and wherein the primary first side of the first adhesive sensor layer is adapted for attachment to the adhesive surface of the base plate when the sensor patch is used in a second configuration, a second adhesive sensor layer forming the second side of the sensor patch, wherein a primary second side of the second adhesive sensor layer is adapted for attachment to the skin surface of the user when the sensor patch is used in the second configuration, and wherein the primary second side of the second adhesive sensor layer is adapted for attachment to the adhesive surface of the base plate when the sensor patch is used in the first configuration, and a monitor interface coupled to both the first part of the plurality of electrodes exposed on the first sensor side and the second part of the plurality of electrodes exposed on the second sensor side, thereby enabling a monitor device connected thereto to measure the plurality of electrodes on both sensor sides.

2. The sensor patch according to claim 1, wherein a primary first sensor part of the first electrode is exposed on the first sensor side and a secondary first sensor part of the first electrode is exposed on the second sensor side, and wherein a primary second sensor part of the second electrode is exposed on the first sensor side and a secondary second sensor part of the second electrode is exposed on the second sensor side.

3. The sensor patch according to claim 2, wherein the sensor assembly comprises a support layer, and wherein the first electrode and the second electrode extend from the first sensor side of the sensor assembly to the second sensor side of the sensor assembly through the support layer.

4. The sensor patch according to claim 3, wherein the first electrode comprises one or more electrically conductive first threads sewn on the support layer.

5. The sensor patch according to claim 3, wherein the support layer is a textile fabric.

6. The sensor patch according to claim 1, wherein the plurality of electrodes includes a third electrode and a fourth electrode forming a second sensor, and wherein a primary first sensor part of the first electrode is exposed on the first sensor side and a primary second sensor part of the second electrode is exposed on the first sensor side, and wherein a primary third sensor part of the third electrode is exposed on the second sensor side and a primary fourth sensor part of the fourth electrode is exposed on the second sensor side.

7. The sensor patch according to claim 6, wherein the sensor assembly comprises a support layer, and wherein the first electrode and the second electrode are arranged on a first side of the support layer and the third electrode and the fourth electrode are arranged on a second side of the support layer.

8. The sensor patch according to claim 7, wherein the first electrode and the second electrode are printed on the first side of the support layer, and wherein the third electrode and the fourth electrode are printed on the second side of the support layer.

9. The sensor patch according to claim 6, wherein the sensor assembly comprises a first support layer and a second support layer, and wherein the first electrode and the second electrode are arranged on a first side of the first support layer and the third electrode and the fourth electrode are arranged on a second side of the second support layer, and wherein a second side of the first support layer is arranged to face a first side of the second support layer.

10. The sensor patch according to claim 9, wherein the second side of the first support layer and the first side of the second support layer are bonded together.

11. The sensor patch according to claim 9, wherein the first electrode and the second electrode are printed on the first side of the first support layer, and wherein the third electrode and the fourth electrode are printed on the second side of the second support layer.

12. The sensor patch according to claim 1, wherein the first adhesive sensor layer and/or the second adhesive sensor layer comprises hydrocolloids.

13. The sensor patch according to claim 1, comprising a first sensor release liner arranged to protect the primary first surface of the first adhesive sensor layer and configured to be peeled off by the user.

14. The sensor patch according to claim 1, comprising a second sensor release liner arranged to protect the primary second surface of the second adhesive sensor layer and configured to be peeled off by the user.

15. The sensor patch according to claim 1, wherein the first electrode forms a first loop surrounding the centre point and the second electrode forms a second loop surrounding the centre point, and wherein a radial distance from the centre point to the second loop is less than the radial distance from the centre point to the first loop.

16. The sensor patch according to claim 1, wherein the first adhesive sensor layer comprises a plurality of first sensor point openings, each of the plurality of first sensor point openings overlapping a part of one of the plurality of electrodes to form a sensor point.

17. The sensor patch according to claim 1, wherein the second adhesive sensor layer comprises a plurality of second sensor point openings, each of the plurality of second sensor point openings overlapping a part of one of the plurality of electrodes to form a sensor point.

18. The sensor patch according to claim 1, wherein:

the monitor interface is configured to mechanically couple with the monitor device at the second side of the sensor patch when the sensor patch is used in the first configuration; and the monitor interface is configured to mechanically couple with the monitor device at the first side of the sensor patch when in the second configuration.

19. A method for manufacturing a sensor patch having a first side and a second side and being adapted for attachment to an adhesive surface of a base plate for a skin surface appliance wherein the adhesive surface of the base plate is adapted for attachment of the base plate to the skin surface of a user, the method comprising:

laying out a layer of a first adhesive sensor material for forming a first adhesive sensor layer of the sensor patch having a primary first side and a secondary first side;

laying out a layer of a second adhesive sensor material for forming a second adhesive sensor layer of the sensor patch having a primary second side and a secondary second side;

providing a sensor assembly comprising a plurality of electrodes including a first electrode and a second electrode for forming a first sensor, the sensor assembly having a first sensor side and a second sensor side, and at least a first part of the plurality of electrodes being exposed on the first sensor side and at least a second part of the plurality of electrodes being exposed on the second sensor side, wherein each sensor of the first part of the plurality of electrodes exposed on the first sensor side corresponds to a sensor of the second part of the plurality of electrodes exposed on the second sensor side;

arranging the sensor assembly between the secondary first side of the first adhesive sensor layer and the secondary second side of the second adhesive sensor layer, such that the first sensor side of the sensor assembly is facing the secondary first side of the first adhesive sensor layer and the second sensor side of the sensor assembly is facing the secondary second side of the second adhesive sensor layer, and providing a monitor interface coupled to both the first part of the plurality of electrodes exposed on the first sensor side and the second part of the plurality of electrodes exposed on the second sensor side, thereby enabling a monitor device connected thereto to measure the plurality of electrodes on both sensor sides.

20. The method according to claim 19, wherein providing the sensor assembly comprises arranging the first electrode and the second electrode on a support layer such that the first electrode and the second electrode extend from the first sensor side of the sensor assembly to the second sensor side of the sensor assembly through the support layer.

21. The method according to claim 20, wherein providing the sensor assembly comprises sewing one or more electrically conductive first threads on the support layer to form the first electrode extending from the first sensor side of the sensor assembly to the second sensor side of the sensor assembly through the support layer.

22. The method according to claim 19, wherein providing the sensor assembly comprises arranging the first electrode and the second electrode on a first side of a support layer and arranging a third electrode and a fourth electrode for forming a second sensor on a second side of the support layer.

23. The method according to claim 19, wherein providing the sensor assembly comprises arranging the first electrode and the second electrode on a first side of a first support layer and arranging a third electrode and a fourth electrode for forming a second sensor on a second side of a second support layer.

24. The method according to claim 19, comprising providing a second sensor release liner, and wherein laying out the layer of the second adhesive sensor material comprises laying out the layer of the second adhesive sensor material on a first side of the second sensor release liner.

25. A sensor patch for attachment between an adhesive surface of a base plate and a skin surface of a user, the sensor patch comprising:

a first adhesive layer forming a first side of the sensor patch and a second adhesive layer forming a second side of the sensor patch, wherein the sensor patch is adapted to adhere between the base plate the skin surface of the user according to:

a first configuration where the first adhesive layer attaches to the adhesive surface of the base plate and the second adhesive layer attaches to the skin surface of the user, and a second configuration where the first adhesive layer attaches to the skin surface of the user and the second adhesive layer attaches to the adhesive surface of the base plate;

a sensor assembly comprising a first set of sensors exposed on a first side of a sensor patch, each sensor of the first set having a corresponding sensor in a second set of sensors exposed on a second side of the sensor patch; and a monitor interface coupled to both the first set of sensors and the second set of sensors, thereby enabling a monitor device removably connected thereto to measure the sensor assembly from both the first side and the second side.

* * * * *